United States Patent
Campochiaro et al.

(10) Patent No.: US 12,078,641 B2
(45) Date of Patent: Sep. 3, 2024

(54) BIOMARKERS USEFUL IN THE TREATMENT OF SUBJECTS HAVING DISEASES OF THE EYE

(71) Applicant: The Johns Hopkins University, Baltimore, MD (US)

(72) Inventors: Peter A. Campochiaro, Baltimore, MD (US); Lili Lu, Joppa, MD (US)

(73) Assignee: The Johns Hopkins University, Baltimore, MD (US)

( * ) Notice: Subject to any disclaimer, the term of this patent is extended or adjusted under 35 U.S.C. 154(b) by 417 days.

(21) Appl. No.: 17/582,286

(22) Filed: Jan. 24, 2022

(65) Prior Publication Data

US 2022/0146533 A1 May 12, 2022

Related U.S. Application Data

(62) Division of application No. 15/523,657, filed as application No. PCT/US2015/060172 on Nov. 11, 2015, now Pat. No. 11,268,964.

(Continued)

(51) Int. Cl.
*G01N 33/68* (2006.01)
*G01N 33/50* (2006.01)
*G01N 33/573* (2006.01)

(52) U.S. Cl.
CPC .. *G01N 33/6893* (2013.01); *C12Y 115/01001* (2013.01); *G01N 33/50* (2013.01);
(Continued)

(58) Field of Classification Search
CPC .......... A61P 27/02; A61P 27/10; A61P 39/06; C12Y 115/01001; G01N 2333/90283; G01N 2800/164; G01N 2800/52; G01N 2800/56; G01N 2800/7009; G01N 33/50; G01N 33/573; G01N 33/6827; G01N 33/6893
See application file for complete search history.

(56) References Cited

U.S. PATENT DOCUMENTS

2003/0027745 A1  2/2003  Repine
2005/0112572 A1  5/2005  Pincemail et al.
(Continued)

FOREIGN PATENT DOCUMENTS

AU  2012324752      5/2014
EP   1975621 A1   10/2008
(Continued)

OTHER PUBLICATIONS

Bean, et al., "Comparative evaluation of antioxidant reactivity within obstructed and control rabbit urinary bladder tissue using FRAP and CUPRAC assays," Molecular and Cellular Biochemistry (Nov. 29, 2008) 323(1-2):139-142.
(Continued)

*Primary Examiner* — Savitha M Rao
(74) *Attorney, Agent, or Firm* — Edwin S. Flores; Daniel J. Chalker; Chalker Flores, LLP

(57) ABSTRACT

The present invention provides biomarkers of oxidative stress in subjects with retinitis pigmentosa, age-related macular degeneration, diabetic retinopathy, Fuchs' dystrophy, diabetic macular edema (DME), geographic atrophy, Stargardt's disease, or retinal vein occlusion (RVO), and their use in identifying subjects in need of treatment and methods for staging the severity of the disease.

6 Claims, 2 Drawing Sheets

Related U.S. Application Data

(60) Provisional application No. 62/078,138, filed on Nov. 11, 2014, provisional application No. 62/188,377, filed on Jul. 2, 2015.

(52) U.S. Cl.
CPC ....... *G01N 33/573* (2013.01); *G01N 33/6827* (2013.01); *G01N 2333/90283* (2013.01); *G01N 2800/164* (2013.01); *G01N 2800/52* (2013.01); *G01N 2800/56* (2013.01); *G01N 2800/7009* (2013.01)

(56) References Cited

U.S. PATENT DOCUMENTS

| | | | |
|---|---|---|---|
| 2012/0142550 | A1 | 6/2012 | Zehnder et al. |
| 2012/0150029 | A1 | 6/2012 | Debuc |
| 2013/0303436 | A1 | 11/2013 | Wilson |

FOREIGN PATENT DOCUMENTS

| | | | |
|---|---|---|---|
| WO | 2003016527 | A2 | 2/2003 |
| WO | 2013057354 | A1 | 4/2013 |
| WO | 2014100361 | A1 | 6/2014 |

OTHER PUBLICATIONS

Campochiaro, et al. "Is there Excess Oxidative Stress and Damage in Eyes of Patients with Retinitis Pigmentosa" Antioxidants Redox Signaling, (2015) 23(7):643-648.

Campochiaro, et al. "The Mechanism of Cone Cell Death in Retinitis Pigmentosa", Progress in Retinal and Eye Research (2018), 62:24-37, available online Sep. 27, 2017.

Dalle-Donne, et al. "Protein carbonyl groups as biomarkers of oxidative stress" Clinica Chimica Acta 329 (2003) 23-38, 16 pp.

European Patent Office, Extended European Search Report for EP 15858590.1 dated May 2, 2018, 13 pp.

European Patent Office, Communication pursuant to Article 94(3) EPC for EP 15858590.1 dated May 17, 2019, 6 pp.

Grinberg, et al. "N-acetylcysteine amide, a novel cell-permeating thiol, restores cellular glutathione and protects human red blood cells from oxidative stress" Free Radical Biology Medicine 38 (2005) 136-145.

Japan Patent Office, Notification of Reasons for Refusal for Patent Appl. No. 2017-544573 dated Aug. 19, 2019, 4 pp.

Japan Patent Office, Notification of Reasons for Refusal for Patent Appl. No. 2020-082163 dated May 10, 2021, 5 pp.

Jones, "Extracellular Redox State: Refining the Definition of Oxidative Stress in Aging," Rejuvenation Research (2006), 9(2):169-181.

Komeima, et al., "Antioxidants reduce cone cell death in a model of retinitis pigmentosa." PNAS, (Jul. 25, 2006), 103(30):11300-11305.

Lu, et al., "Effects of Different Types of Oxidative Stress in RPE Cells," J Cell Phys (2006), 206(1):119-125.

Martinez-Fernandez De La Camara, et al., Altered Antioxidant-Oxidant Status in Aqueous Humor and Peripheral Blood of Patents with Retinitis Pigmentosa, PLOS ONE (Sep. 2013), 8(9):E74223.

Riley, et al., "Glutathione in the aqueous humor of human and other species." Investigative ophthalmology visual science, (Jan. 1980), 9(1):94-96.

Shen, et al., "Oxidative damage in age-related macular degeneration," Histology and Histopathology (2007), 22 (12):1301-1308.

Shinichi, et al. "Overexpression of 1-15 SOD in retina: Need for increase in HO-detoxifying enzyme in same cellular compartment", Free Radical Biology and Medicine, vol. 51, No. 7, Jun. 6, 2011 (Jun. 6, 2011), pp. 1347-1354, XP028276241, Elsevier Inc, US ISSN: 0891-5849, 001: 10.1016/J.FREERADBIOMED.2011.06.010.

United States Patent & Trademark Office (ISA), International Search Report and Written Opinion PCT/US2015/060172 Dated Apr. 13, 2016, 12 pg.

Usui, et al., "Overexpression of SOD in retina: Need for increase in H2O2-detoxifying enzyme in same cellular compartment," Free Radical Biology and Medicine (Jul. 2011), 51(7):1347-1354, available online Jul. 5, 2011.

BIOMARKERS USEFUL IN THE TREATMENT OF SUBJECTS HAVING DISEASES OF THE EYE

CROSS-REFERENCE TO RELATED APPLICATIONS

This application is a divisional of Ser. No. 15/523,657 filed on May 1, 2017, which is a U.S. 371 National Phase Application from PCT No. PCT/US2015/060172 international filing date of Nov. 11, 2015, title Biomarkers Useful in the Treatment of Subjects Having Disease of the Eye, and claims benefit of U.S. Provisional Ser. No. 62/078,138, filed on Nov. 11, 2014 and U.S. Provisional Ser. No. 62/188,377, filed on Jul. 2, 2015.

TECHNICAL FIELD OF THE INVENTION

The present invention relates in general to the field of methods for detecting oxidative stress, and more particularly, to novel methods for detecting oxidative stress in body fluids.

BACKGROUND OF THE INVENTION

Retinitis Pigmentosa (RP) is the term used for a genetically heterogenous group of inherited retinal degenerations. Findings may be limited to the eyes or the eye findings may be part of a syndrome the most common of which is Usher's Syndrome in which deafness accompanies the retinal disease. In each disorder the inciting event is a mutation that leads to the death of rod photoreceptors, initially causing night blindness. Rods are the major consumers of oxygen in the retina and the loss of rods causes an increase in the tissue oxygen level in the outer retina. This activates NADPH oxidase causing accumulation of superoxide radicals in the cytosol and also increases their generation in mitochondria of cones. The excess superoxide radicals overwhelm superoxide dismutase 1 (SOD1) and SOD2 and cause a chain reaction by which other free radicals are generated including some that are even more damaging than superoxide radicals, such as hydroxyl radicals and peroxynitrite. The free radicals attack proteins, lipids, and DNA causing specific modifications that indicate that oxidative damage has occurred. Oxidative damage to lipids results in lipid hydroperoxides that break down to form 4-hydroxynonenal, malondialdehyde (MDA), and acrolein. The most common modification to proteins from oxidative damage is the formation of carbonyl adducts. These modifications can impair the function of macromolecules and while there are endogenous repair processes, they are overwhelmed by severe oxidative stress resulting in reduced cellular function and eventually apoptosis. After rods are eliminated from the photoreceptor layer, oxidative stress in the outer retina is severe and leads to gradual cone cell death usually starting in the midperiphery where cone density is low and then spreading peripherally and posteriorly. The posterior spread of cone death results in constriction of the visual field and eventually a central island of vision and its elimination causes blindness. Clinical signs of RP include pigmentary changes in the retina, often around blood vessels and characterized as "bone spicule-like pigmentation", constriction of retinal vessels, and optic disc pallor. Spectral domain optical coherence tomography can show thinning of the retina in areas of photoreceptor cell loss and with segmentation the loss is seen in the outer nuclear layer. Visual field testing shows constriction of the visual fields and electroretinograms show reduced a- and b-wave amplitudes.

Currently, there is no approved therapy that stops the evolution of the disease or restores vision. The therapeutic approach is restricted to slowing down the degenerative process by sunlight protection and vitamin A supplementation, treating complications (cataract and macular edema), and helping patients to cope with the social and psychological impact of blindness. Although the Argis II Retinal Prosthesis System was approved by FDA in 2013 as an implanted device to treat adults with severe RP, it only produces the sensation of light, thereby helping patients identify the location or movement of objects and people; the device is not disease modifying.

In order to test new treatments, it is necessary to have robust measures of disease progression. The most widely accepted functional measure of disease progression is loss of visual field; however, there are several ways to assess visual fields and their value may differ at different stages of the disease. Goldman visual fields provide a good assessment of peripheral visual fields and are useful during the early stages of cone cell loss. Assessment of retinal function by full field ERGs is also most useful in early stage disease because signals are low and often unrecordable in later stage disease. Automated measures of retinal sensitivity provide measurements on posterior retina, which is normal early in the disease, but in later stage disease is more sensitive and quantitative than Goldman visual fields.

Determining the annual rate of change in the width of the central area of intact inner segment ellipsoid zone by spectral domain OCT provides a fairly sensitive anatomic measure of disease progression in relatively advanced disease. A problem shared by all of these outcome measures is that their rate of change over time is low necessitating long term clinical trials to have a chance of detecting treatment effects.

As such, the identification and development of biomarkers that could serve as interim readouts of drug activity, bioavailability, and compliance would be a major benefit for planning and carrying out clinical trials.

SUMMARY OF THE INVENTION

The present inventors have determined that the ongoing oxidative stress in patients with RP causes oxidative damage to secreted macromolecules as well as those that are retained within cells. Therefore novel markers of oxidative stress should be detectable in aqueous humor and serum of patients with, e.g., retinitis pigmentosa, age-related macular degeneration, diabetic retinopathy, myopia, high myopia, Fuchs' dystrophy, diabetic macular edema (DME), geographic atrophy, Stargardt's disease, or retinal vein occlusion (RVO), and should be greater than the baseline levels in aqueous humor and serum from normal control patients. Furthermore, as cone death progresses, oxidative stress should increase and therefore the level of any particular marker of oxidative damage is likely to increase in an RP patient over time, and in a population of RP patients there is a positive correlation between level of an oxidative damage marker and stage of disease.

Thus, in one aspect, the present invention provides methods for assessing the severity or stage of RP in a patient diagnosed with the disease by measuring markers, which indicate increasing or decreasing oxidative stress in the aqueous humor and serum of patients. The methods disclosed herein can also be used to monitor the progression of the disease in a patient over time and determine whether a course of treatment is effective in slowing or stopping the progression of the disease in the eye.

In accordance with an embodiment, the present invention provides a method for quantifying or staging the severity of disease of the eye in a subject diagnosed as having an eye disease caused by oxidative stress or damage, including but not limited to, retinitis pigmentosa, age-related macular degeneration, diabetic retinopathy, myopia, high myopia, Fuchs' dystrophy, diabetic macular edema (DME), geographic atrophy, Stargardt's disease, or retinal vein occlusion (RVO), comprising: a) obtaining a biological sample from the subject; b) providing a control biological sample; c) measuring one or more of the following: cupric reducing antioxidant capacity, GSH/GSSG ratio, and carbonyl adduct level in the sample of a) and b); d) comparing the one or more measurements of c) in the sample from the subject to the control sample; and e) quantifying or staging the severity of disease in the subject as progressing in stage, or increasing in severity, if the levels of cupric reducing antioxidant capacity and/or GSH/GSSG ratio is reduced relative to the control sample, and/or if the levels of carbonyl adduct level is elevated relative to the control sample.

Therefore, in accordance with another embodiment, the present invention provides a method for treating a subject having eye damage caused by oxidative stress or damage, e.g., retinitis pigmentosa, age-related macular degeneration, diabetic retinopathy, myopia, high myopia, or Fuchs' dystrophy, comprising: a) obtaining a biological sample from the subject; b) providing a control biological sample; c) measuring one or more of the following: cupric reducing antioxidant capacity, GSH/GSSG ratio, carbonyl adduct level in the sample of a) and b); d) comparing the one or more measurements of c) in the sample from the subject to the control sample; e) quantifying or staging the severity of disease in the subject as progressing in stage, or increasing in severity, if the levels of cupric reducing antioxidant capacity and/or GSH/GSSG ratio is reduced relative to the control sample, and/or if the levels of carbonyl adduct level is elevated relative to the control sample; and f) selecting a course of treatment for the disease in the subject which is based on the stage or severity of disease indicated in e).

Therefore, in accordance with another embodiment, the present invention provides a method for quantifying oxidative stress comprising: a) obtaining a biological sample from the subject; b) providing a control biological sample; c) measuring one or more of the following: cupric reducing antioxidant capacity, GSH/GSSG ratio, and carbonyl adduct level in the sample of a) and b); and d) comparing the one or more measurements of c) in the sample from the subject to the control sample, wherein an increase in carbonyl adduct level, a ratio of GSH to GSSG is reduced, and/or a reduction in cupric antioxidant capacity is indicative of oxidative stress. In one aspect, the sample is from the aqueous humor of the eye of the subject. In another aspect, the sample is from the blood or plasma of the subject. In another aspect, the sample is obtained from a subject suspected of having retinitis pigmentosa, age-related macular degeneration, diabetic retinopathy, myopia, high myopia, Fuchs' dystrophy, diabetic macular edema (DME), geographic atrophy, Stargardt's disease, or retinal vein occlusion (RVO). In another aspect, the levels of protein carbonyl levels are determined by EIA (enzyme immunoassay), ELISA (enzyme linked immunosorbent assay), RIA (radioimmunoassay), indirect competitive immunoassay, direct competitive immunoassay, non-competitive immunoassay, sandwich immunoassay, agglutination assay, Western blot assay, slot blot assay, fluorescence polarization, latex agglu-tination, lateral flow assay, immunochromatographic assay, immunochips, dip stick immunotesting, or bead-based technology. In another aspect, the method further comprises the step of measuring cone cell death upon a finding of an increase in carbonyl adduct level, a ratio of GSH to GSSG is reduced, and/or a reduction in cupric antioxidant capacity is indicative of oxidative stress in the subject.

Therefore, in accordance with another embodiment, the present invention provides a kit for determining the oxidative stress comprising: a) a first container for a biological sample from the subject; b) a second container for a control biological sample; c) one or more vials that comprise reagents to determine: cupric reducing antioxidant capacity, GSH/GSSG ratio, and carbonyl adduct level in the sample of a) and b); and d) instructions for comparing the one or more measurements of c) in the sample from the subject to the control sample, wherein an increase in carbonyl adduct level, a ratio of GSH to GSSG is reduced, and/or a reduction in cupric antioxidant capacity is indicative of oxidative stress. In one aspect, the sample is from the aqueous humor of the eye of the subject. In another aspect, the biological is from a subject suspected of having retinitis pigmentosa, age-related macular degeneration, diabetic retinopathy, myopia, high myopia, Fuchs' dystrophy, diabetic macular edema (DME), geographic atrophy, Stargardt's disease, or retinal vein occlusion (RVO). In another aspect, the levels of protein carbonyl levels are determined by EIA (enzyme immunoassay), ELISA (enzyme linked immunosorbent assay), RIA (radioimmunoassay), indirect competitive immunoassay, direct competitive immunoassay, non-competitive immunoassay, sandwich immunoassay, agglutination assay, Western blot assay, slot blot assay, fluorescence polarization, latex agglutination, lateral flow assay, immunochromatographic assay, immunochips, dip stick immunotesting, or bead-based technology. In another aspect, the instructions are used to determine if the levels of cupric reducing antioxidant capacity and/or GSH/GSSG ratio is reduced relative to the control sample, and/or if the levels of carbonyl adduct level is elevated relative to the control sample then the disease is identified as progressing in stage, or increasing in severity, or if the levels of cupric reducing antioxidant capacity and/or GSH/GSSG ratio is elevated relative to the control sample, and/or if the levels of carbonyl adduct level is reduced relative to the control sample then the disease is identified, the decease is seen as reducing in stage, or the disease is decreasing in severity. In another aspect, the increase in carbonyl adduct level, the ratio of GSH to GSSG is reduced, and/or a reduction in cupric antioxidant capacity is indicative of cone cell death in Retinitis Pigmentosa.

Figure 3:
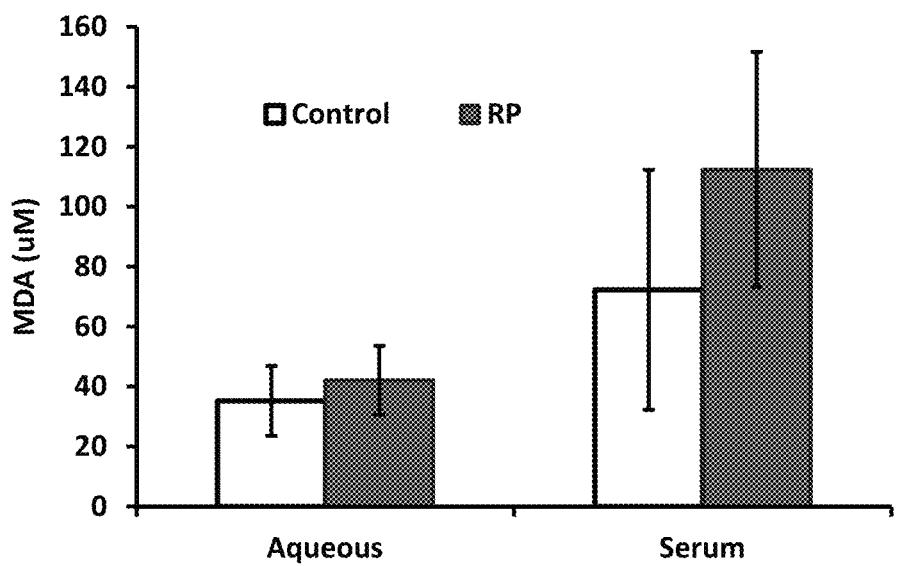

FIG. 3 is a graph that shows a comparison between retinitis pigmentosa (RP) and control patients in malondialdehyde (MDA) level in aqueous and serum. Aqueous samples from 7 RP and 6 control patients and serum samples from 8 RP and 7 controls were assayed for MDA. The bars represent the mean (±standard deviation). Statistical comparisons by Student's unpaired t-test showed no statistically significant differences.

Figure 4:
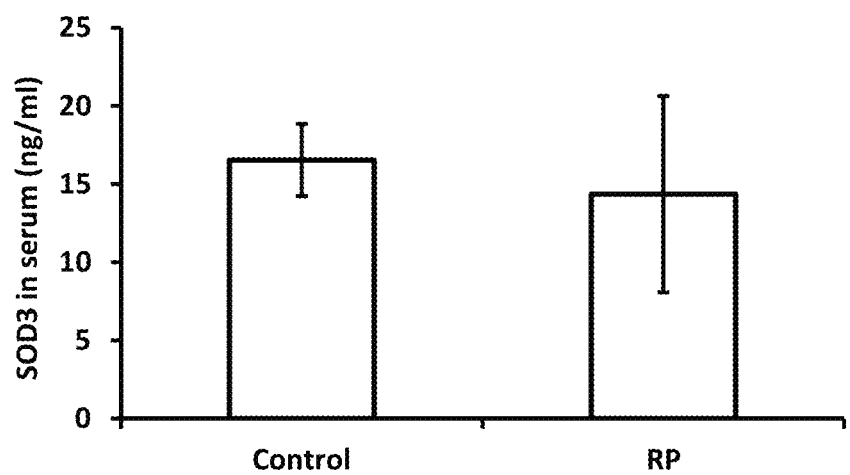

FIG. 4 is a comparison between retinitis pigmentosa (RP) and control patients in superoxide dismutase 3 (SOD3) level in serum. Serum samples were from 8 RP and 8 control patients were assayed for SOD3. Each bar represents the mean (±standard deviation) SOD3 per ml of sample. Statistical comparison by Student's unpaired t-test showed no significant difference.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. RP: retinitis pigmentosa; GSH: reduced glutathione; GSSG: oxidized glutathione; NADPH: nicotinamide adenine dinucleotide phosphate; DNA: deoxyribonucleic acid; MDA: malondialdehyde; ELISA: enzyme-linked immunosorbent assay; SOD3: superoxide dismutase 3; TAC: total antioxidant capacity; PBS: phosphate-buffered saline.

The present invention includes a biomarker and methods for detecting the presence of retinal and eye diseases that includes oxidative stress.

As used herein, the term "Retinitis Pigmentosa" or "RP" refers to a genetically heterogenous group of inherited retinal degenerations that leads to the death of rod photoreceptors, initially causing night blindness. Rods are the major consumers of oxygen in the retina and the loss of rods causes an increase in the tissue oxygen level in the outer retina.

As used herein, the term "Age-related macular degeneration" or "AMD" refers to a disease of the retina that includes the presence of small accumulations of extracellular material in the retina called drusen and also includes oxidative stress, as shown in the Age-Related Eye Disease Study (AREDS) study. While small drusen are not uncommon between the ages of 40 to 50, large drusen are typically indicative of AMD. The mechanism for the formation of drusen in AMD is not completely understood, but their presence interferes with the supply of nutrients and oxygen to rods and cones.

As used herein, the term "diabetic retinopathy" refers to a common complication of diabetes that results from, e.g., non-resolving vitreous hemorrhage, traction retinal detachment or diabetic maculopathy, which are often the result of retinal capillary closure or leakage and include oxidative stress. While the degree of complications can vary, diabetic complications affecting the retina lead to severe loss of vision. Retinal disease is one of several complications of diabetes and is primarily the result of disruption of small blood vessels and the uncontrolled growth of new vessels. In some situations, these changes affect the macula, which is the area of the retina that is specialized to color and visual acuity.

As used herein, the term "Fuchs' dystrophy" or "Fuchs' endothelial dystrophy" is a degenerative disease of the corneal endothelium with an association with oxidative stress that shows an accumulation of focal outgrowths and thickening of Descemet's membrane, which leads to corneal edema and vision loss. Other diseases that can be measured with the present invention include diabetic macular edema (DME), geographic atrophy, Stargardt's disease, or retinal vein occlusion (RVO).

Tissues combat oxidative stress through the endogenous antioxidant defense system, which has several components. Individuals vary in the effectiveness of their antioxidant defense system based upon their genetic makeup. Patients also vary with regard to antioxidants in their diet. Patients with RP who have a particularly effective antioxidant defense system and/or an antioxidant-rich diet should have a slower rate of cone cell loss and hence progression of disease. This variability in disease progression adds "noise" to attempts to assess the impact of a treatment on disease progression. Assessment of the reducing power, also known as total antioxidant capacity (TAC) of a tissues provides a readout of the endogenous antioxidant defense system, the level of exogenous antioxidants in the tissue, and the current level of oxidative stress (because antioxidant capacity is reduced by oxidative stress). It can therefore provide an assessment of how well the individual is coping with the current load of oxidative stress in the tissue. The addition of an antioxidant therapy should increase the TAC in the target tissue if it has a chance of reducing oxidative damage in the tissue. Thus, in accordance with some embodiments, increase in TAC above baseline can provide assessments of compliance and bioavailability, and serve as a biomarker to predict therapeutic effect.

The ferric reducing ability of plasma (FRAP) assay is advantageous because it is relatively inexpensive, and convenient (Anal. Biochem. 1996; 239:70-6). Measurement of TAC using FRAP decreases with aging and at any age, there is correlation between antioxidant capacity and oxidative damage in various tissues (Rejuvenation Res. 2006; 9:470-4; Free Radic. Biol. Med. 2002; 33:597-604; Ann. Biol. Clin. 2001; 59:453-9). The cupric reducing antioxidant capacity (CUPRAC) method is similar to FRAP, but has better kinetics and is more reproducible (Free Radic. Res. 2005; 39:949-61; Mol. Cell Biochem. 2009; 323:139-42). Reduced glutathione (GSH) is a major intracellular non-protein —SH compound and is the most important intracellular hydrophilic antioxidant. Under oxidative conditions, GSH is reversibly oxidized to glutathione disulfide (GSSG) and under reducing conditions, GSH is regenerated. Thus the GSH/GSSG ratio provides a measure of antioxidant status similar to antioxidant capacity (Rejuvenation Res. 2006; 9:169-81).

Thus, in accordance with one or more embodiments, the present invention provides biomarkers, such as CUPRAC and GSH/GSSH ratio, which are shown to be reduced in the aqueous humor with RP and the level of reduction correlates with the increased stage of cone cell loss.

In accordance with an embodiment, the present invention provides a method for quantifying or staging the severity of disease in a subject diagnosed with a disease or condition that is caused or exacerbated by oxidative stress, such as Retinitis Pigmentosa, macular degeneration (e.g., age-related macular degeneration), diabetic retinopathy, myopia, high myopia, or Fuchs' dystrophy, comprising: a) obtaining a biological sample from the subject; b) providing a control biological sample; c) measuring one or more of the following: cupric reducing antioxidant capacity, GSH/GSSG ratio, and carbonyl adduct level in the sample of a) and b); d) comparing the one or more measurements of c) in the sample from the subject to the control sample; and e) quantifying or staging the severity of disease in the subject as progressing in stage, or increasing in severity, if the levels of cupric reducing antioxidant capacity and/or GSH/GSSG ratio is reduced relative to the control sample, and/or if the levels of carbonyl adduct level is elevated relative to the control sample.

Therefore, in accordance with another embodiment, the present invention provides a method for treating a subject having Retinitis Pigmentosa comprising: a) obtaining a biological sample from the subject; b) providing a control biological sample; c) measuring one or more of the following: cupric reducing antioxidant capacity, GSH/GSSG ratio, carbonyl adduct level in the sample of a) and b); d) comparing the one or more measurements of c) in the sample from the subject to the control sample; e) quantifying or staging the severity of disease in the subject as progressing in stage, or increasing in severity, if the levels of cupric reducing antioxidant capacity and/or GSH/GSSG ratio is reduced relative to the control sample, and/or if the levels of carbonyl adduct level is elevated relative to the control sample; and f) selecting a course of treatment for the disease in the subject which is based on the stage or severity of disease indicated in e).

In a further embodiment, the present invention provides a method for monitoring the treatment of a subject having Retinitis Pigmentosa comprising: a) obtaining a biological sample from the subject; b) providing a control biological sample; c) measuring one or more of the following: cupric reducing antioxidant capacity, GSH/GSSG ratio, carbonyl adduct level in the sample of a) and b); d) comparing the one or more measurements of c) in the sample from the subject to the control sample; e) determining the stage or the severity of disease in the subject, wherein if the levels of cupric reducing antioxidant capacity and/or GSH/GSSG ratio is reduced relative to the control sample, and/or if the levels of carbonyl adduct level is elevated relative to the control sample then the disease is identified as progressing in stage, or increasing in severity, or if the levels of cupric reducing antioxidant capacity and/or GSH/GSSG ratio is elevated relative to the control sample and/or if the levels of carbonyl adduct level is reduced relative to the control sample then the disease is identified as reducing in stage, or decreasing in severity; f) selecting a course of treatment for the disease in the subject which is based on the stage or severity of disease indicated in e); and g) after administration of the course of treatment to the subject, repeating steps a)-f) one or more times.

In accordance with one or more embodiments, the present inventors have determined that because oxidative stress is the primary insult to cones in the eye, the amount of oxidative damage measured on macromolecules in the aqueous humor will correlate with ongoing oxidative damage to cones, and therefore these provide a measure of disease activity in the eye of a subject with RP. As such, the importance of these inventive markers is that at any stage of disease, the clinician's treatment objective is to reduce disease activity and hence ongoing damage. Therefore the present invention allows one of skill in the art to determine if a particular treatment is having the desired effect, in a much shorter time-frame, without waiting to see if it slows the loss of cone function in the subject.

For example, after selecting a cohort of patients having RP, one of skill in the art would measure one or more of the following markers: cupric reducing antioxidant capacity, GSH/GSSG ratio, and carbonyl adduct level in samples from the subject before treatment as an indicator of baseline activity. The treatment would then begin with n-acetylcystine amide, or another suitable treatment, and then further samples would be taken at various time points during therapy. If the markers show a decrease in oxidative stress, that will correlate with a decrease in disease activity. Then over time, the reduction in disease activity markers should correlate with reduction in rate of loss of cone function in the subject.

In another aspect, use of the cupric reducing antioxidant capacity, GSH/GSSG ratio, and carbonyl adduct level in samples from the subject can be used to screen for other potential drugs which can reduce oxidative stress in the eye.

An "agent" is understood herein to include a therapeutically active compound or a potentially therapeutic active compound, e.g., an antioxidant. An agent can be a previously known or unknown compound. As used herein, an agent is typically a non-cell based compound, however, an agent can include a biological therapeutic agent, e.g., peptide or nucleic acid therapeutic, e.g., siRNA, shRNA, cytokine, antibody, etc.

As used herein "amelioration" or "treatment" is understood as meaning to lessen or decrease at least one sign, symptom, indication, or effect of a specific disease or condition. For example, amelioration or treatment of retinitis pigmentosa (RP) can be to reduce, delay, or eliminate one or more signs or symptoms of RP including, but not limited to, a reduction in night vision, a reduction in overall visual acuity, a reduction in visual field, a reduction in the cone density in one or more quadrants of the retina, thinning of retina, particularly the outer nuclear layer, reduction in a- or b-wave amplitudes on scotopic or photopic electroretinograms (ERGs); or any other clinically acceptable indicators of disease state or progression. Amelioration and treatment can require the administration of more than one dose of an agent, either alone or in conjunction with other therapeutic agents and interventions. Amelioration or treatment does not require that the disease or condition be cured.

An "antioxidant" as used herein is understood as a molecule capable of slowing or preventing the oxidation of other molecules. Oxidation is a chemical reaction that transfers electrons from a substance to an oxidizing agent. Such reactions can be promoted by or produce superoxide anions or peroxides. Oxidation reactions can produce free radicals, which start chain reactions that damage cells. Antioxidants terminate these chain reactions by removing free radical intermediates, and inhibit other oxidation reactions by being oxidized themselves. As a result, antioxidants are often reducing agents such as thiols, ascorbic acid or polyphenols. Antioxidants include, but are not limited to, α-tocopherol, ascorbic acid, Mn(III)tetrakis (4-benzoic acid) porphyrin, α-lipoic acid, and n-acetylcysteine.

"Co-administration" as used herein is understood as administration of one or more agents to a subject such that the agents are present and active in the subject at the same time. Co-adminsitration does not require a preparation of an admixture of the agents or simultaneous administration of the agents.

The terms "effective amount," or "effective dose" as used herein refer to that amount of an agent to produce the intended pharmacological, therapeutic or preventive result. The pharmacologically effective amount results in the amelioration of one or more signs or symptoms of a disease or condition or the advancement of a disease or condition, or causes the regression of the disease or condition. For example, a therapeutically effective amount preferably refers to the amount of a therapeutic agent that decreases the loss of night vision, the loss of overall visual acuity, the loss of visual field, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject over a defined period of time, e.g., 2 weeks, one month, 2 months, 3 months, 6 months, one year, 2 years, 5 years, or longer. More than one dose may be required to provide an effective dose.

The terms "effective" and "effectiveness" as used herein include both pharmacological effectiveness and physiological safety. Pharmacological effectiveness refers to the ability of the treatment to result in a desired biological effect in the patient.

Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease signs or symptoms, extension of life, improvement in quality of life, or other effect generally recognized as positive by medical doctors familiar with treating the particular type of disease or condition.

"Oxidative stress related ocular disorders" as used herein include, but are not limited to, retinitis pigmentosa, macular degeneration including age related macular degeneration (AMD) both wet and dry, diabetic retinopathy, Lebers optic neuropathy, myopia, high myopia, and optic neuritis.

"Peroxidases" or "a peroxide metabolizing enzyme" are a large family of enzymes that typically catalyze a reaction of the form:

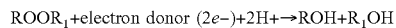

$ROOR_1$+electron donor $(2e-)+2H+\rightarrow ROH+R_1OH$

For many of these enzymes the optimal substrate is hydrogen peroxide, wherein each R is H, but others are more active with organic hydroperoxides such as lipid peroxides. Peroxidases can contain a heme cofactor in their active sites, or redox-active cysteine or selenocysteine residues.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations, particularly phosphate buffered saline solutions which are preferred for intraocular delivery.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperotineal, intraocular, intravitreal, subretinal, and/or other routes of parenteral administration. The specific route of administration will depend, inter alia, on the specific cell to be targeted. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

The term "plurality" is understood to mean more than one. For example, a plurality refers to at least two, three, four, five, or more.

The term "prevention" as used herein is understood as to limit, reduce the rate or degree of onset, or inhibit the development of at least one sign or symptom of a disease or condition particularly in a subject prone to developing the disease or disorder. For example, a subject having a mutation in a gene, such as the opsin gene, is likely to develop RP. The age of onset of one or more symptoms of the disease can sometimes be determined by the specific mutation. Prevention can include the delay of onset of one or more signs or symptoms of RP and need not be prevention of appearance of at least one sign or symptom of the disease throughout the lifetime of the subject. Prevention can require the administration of more than one dose of an agent or therapeutic.

A "small molecule" as used herein is understood as a compound, typically an organic compound, having a molecular weight of no more than about 1500 Da, 1000 Da, 750 Da, or 500 Da. In an embodiment, a small molecule does not include a polypeptide or nucleic acid including only natural amino acids and/or nucleotides.

A "subject" as used herein refers to living organisms. In certain embodiments, the living organism is an animal, in certain preferred embodiments, the subject is a mammal, in certain embodiments, the subject is a domesticated mammal or a primate including a non-human primate. Examples of subjects include humans, monkeys, dogs, cats, mice, rats, cows, horses, goats, and sheep. A human subject may also be referred to as a patient.

A subject "suffering from or suspected of suffering from" as used herein refers to a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions such as RP and age-related macular degeneration (AMD) is within the ability of those in the art. Subjects suffering from, and suspected of suffering from, a specific disease, condition, or syndrome are not necessarily two distinct groups.

A "superoxide dismutase" as used herein, is understood as an enzyme that dismutation of superoxide into oxygen and hydrogen peroxide. Examples include, but are not limited to SOD1, SOD2, and SOD3. SOD1 and SOD3 are two isoforms of Cu—Zn-containing superoxide dismutase enzymes exist in mammals. Cu—Zn-SOD or SOD1, is found in the intracellular space, and extracellular SOD (ECSOD or SOD3) predominantly is found in the extracellular matrix of most tissues.

A "therapeutically effective amount," as used herein refers to an amount of an agent which is effective, upon single or multiple dose administration to the cell or subject, in prolonging the survivability of the patient with such a disorder, reducing one or more signs or symptoms of the disorder, preventing or delaying and the like beyond that expected in the absence of such treatment.

An agent or other therapeutic intervention can be administered to a subject, either alone or in combination with one or more additional therapeutic agents or interventions, as a pharmaceutical composition in mixture with conventional excipient, e.g., pharmaceutically acceptable carrier, or therapeutic treatments.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, PA, 1985), relevant portions incorporated herein by reference.

Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

In some embodiments, the treatment of a subject identified as having RP can include antioxidant therapy, such as N-acetyl cysteine (NAC), N-acetyl cysteine amide (NACA), ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

In other embodiments, the treatment of a subject identified as having RP can include administering an isolated polynucleotide encoding human glutamate cysteine ligase and human glutathione synthase in an expression construct as taught in International Application No. PCT/US2013/076433 and incorporated by reference herein in its entirety.

In some embodiments, the one or more antioxidant agents is administered intraocularly, subretinally, intravitreally, orally, intravenously, intramuscularly, intramedullarily, intrathecally, intraventricularly, transdermaly, subcutaneously, intraperitoneally, intranasally, enterally, topically, sublingually, or rectally.

It will be appreciated that the actual preferred amounts of active compounds or agents used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines.

The agents can, for example, be administered by injection, intraocularly, intravitreally, subretinal, intravenously, intraarterially, subdermally, intraperitoneally, intramuscularly, or subcutaneously; or orally, buccally, nasally, transmucosally, directly to a diseases organ by catheter, topically, or in an ophthalmic preparation, with a dosage ranging from about 0.001 to about 100 mg/kg of body weight, or according to the requirements of the particular drug and more preferably from 0.5-10 mg/kg of body weight. It is understood that when a compound is delivered directly to the eye, considerations such as body weight have less bearing on the dose.

Frequency of dosing will depend on the agent administered, the progression of the disease or condition in the subject, and other considerations known to those of skill in the art. For example, pharmacokinetic and pharmacodynamic considerations for compositions delivered to the eye, or even compartments within the eye, are different, e.g., clearance in the subretinal space is very low. Therefore, dosing can be as infrequent as once a month, once every three months, once every six months, once a year, once every five years, or less. If systemic administration of antioxidants is to be performed in conjunction with administration of expression constructs to the subretinal space, it is expected that the dosing frequency of the antioxidant will be higher than the expression construct, e.g., one or more times daily, one or more times weekly.

Dosing may be determined in conjunction with monitoring of one or more signs or symptoms of the disease, e.g., visual acuity, visual field, night visions, etc. The amount of active ingredient that may be combined with the carrier materials to produce a single dosage form will vary depending upon the host treated and the particular mode of administration. A typical preparation will contain from about 1% to about 95% active compound (w/w).

Alternatively, such preparations contain from about 20% to about 80% active compound. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

In accordance with some embodiments, the methods taught herein are useful for managing the dosage of various RP treatments, as well as determining whether the treatments are having the effect of lowering the oxidative products in the eye, well before any physical measurements of vision are manifested. Thus, the methods of the present invention can be used in conjunction with various RP treatments to better manage the disease.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, TWEEN® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as TWEENs® or SPANs® and/or other similar emulsifying agents or bioavailability enhancers which are commonly used in the manufacture of pharmaceutically acceptable solid, liquid, or other dosage forms may also be used for the purposes of formulation.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

Aqueous and serum MDA, carbonyl content, CUPRAC, and GSH/GSSH will be measured in RP patients and controls. Serum bilirubin is measured in RP patients and controls.

It will be understood by those of skill in the art, that the methods for assessing Aqueous and serum MDA, carbonyl content, CUPRAC, and GSH/GSSH will be measured in RP patients and controls are not limited to any particular assay or method, and can use any known analytical method.

EXAMPLES

Subjects. The study was registered on clinicaltrials.gov (NCT01949623), the protocol was approved by the Johns Hopkins University institutional review board, and all participating patients provided informed consent. The diagnosis of RP was made by a retina specialist with expertise in inherited retinal degenerations (HPS) based upon eye examination, electroretinography, visual field testing, and optical coherence tomography. Nine patients with RP were included in this study. An aqueous sample was obtained by administering topical anesthesia and a drop of 5% povidone iodine into the study eye, placing a lid speculum, inserting a 30-gauge needle on a 1 ml syringe into the anterior chamber at the limbus, and gently aspirating aqueous. Samples were frozen and stored at $-80°$ C. until assayed. A blood sample was also obtained and after clotting, the blood was centrifuged. Serum was placed in a small tube and stored at $-80°$ C. until assayed. Eleven control patients who were undergoing vitreous surgery for macular pucker or macular hole and had no other retinal or ocular disease were included. At the beginning of surgery after the eye was anesthetized and washed with povidone iodine, a 30-gauge needle on a 1 ml syringe was inserted into the anterior chamber at the limbus and of aqueous was aspirated. Serum samples were obtained in 7 of the 11 patients; 2 patients did not have blood drawn due to poor venous access and in 2 patients there was hemolysis making the samples unusable. When aqueous samples were thawed, it was noted that the volume ranged from 50 to 150 µl and not all assays could be done with low volume samples. The protein concentration of each sample was measured with a protein assay kit (Bio-Rad, Hercules, CA) using the manufacturer's instructions.

Measurement of Protein Carbonyl Content. Protein carbonyl content was measured with an OxiSelect Protein Carbonyl ELISA kit (Cell Biolabs, Inc., San Diego, CA) using the manufacturer's instructions. Aqueous samples from 9 patients with RP and 9 control patients were assayed. Serum samples were available from 8 of the patients with RP and 7 control patients. In brief, 50 µl of each sample (aqueous and serum) or protein carbonyl standard was added to a well of a 96-well plate and incubated at 4° C. overnight. All washed throughout the Methods section were done with phosphate-buffered saline (PBS). After washing each well, 100 µl of dinitrophenylhydrazine was added and incubated for 45 minutes at room temperature. After 3 washes, blocking solution was added to each well and the plate was incubated for 1 hour at room temperature. After 3 washes, primary antibody was added to each well and incubated for 1 hour at room temperature. Wells were washed 3 times, secondary antibody was added, and the plate was incubated for 1 hour at room temperature.

Wells were washed 3 times, 100 µl of substrate was added to each well, the plate was incubated at room temperature for 25 minutes, and the reaction was stopped by adding 100 µl of stop solution to each well. Absorbance at 450 nm was read on a plate reader. The readings from the standards were used to generate a standard curve and the protein carbonyl content of each sample in nmol/mg protein was determined by plotting its absorbance value on the standard curve. Each bar represents the mean (±standard deviation) protein carbonyl content per mg protein and statistical comparison was made by Student's unpaired t-test.

Measurement of GSH/GSSG Ratio. There was sufficient aqueous sample volume for the assays for 7 RP patients and 6 control patients. Serum samples were available for 9 RP patients and 7 control patients. The GSH/GSSH ratio was measured by separate measurement of GSH and GSSG. For measurement of GSH, 50 µl of each sample (aqueous or serum), a GSH standard (ranging from 3 to 320 pmol), or a PBS blank were added to a well of a 96-well plate. After addition of 100 µl of a mixture of 2-nitrobenoic acid, NADPH, PBS, and GSH reductase, plates were incubated at room temperature for 2 minutes and then absorbance at 405 nm was read on a plate reader. The absorbance values of the standards were plotted to generate a standard curve, which was used to calculate the GSH level of each sample. For measurement of GSSG, 50 µl of each sample (aqueous or serum), a GSSG standard (ranging from 3 to 320 pmol), or blank PBS buffer were added to a well of a 96-well plate. A mixture of 2 µl of 2-vinylpyridine and 6 µl of triethanolamine was added to each well. After addition to each well of 100 µl of a mixture of 2-nitrobenoic acid, NADPH, PBS and GSH reductase, the plate was incubated at room temperature for 2 minutes, and then absorbance at 405 nm was read on a plate reader. The level of GSSG in each sample was calculated by comparison to the standard curve. The bars represent the mean (±standard deviation) GSH/GSSH ratio and statistical comparison was made by unpaired t-test.

Measurement of MDA. There was sufficient aqueous sample volume for the assays for 7 RP patients and 7 control patients. Serum samples were available for 8 RP patients and 7 control patients. The concentration of MDA in each sample was measured as previously described. Malonaldehyde bisdimethyl (Sigma, Saint Louis, MO) was used to prepare samples with known MDA concentrations between 0 and 20 µM to generate a standard curve. Ten µl of serum or 15 µl of aqueous was added to 90 µl or 85 µl of 100% methanol and then 200 µl of 20% trichloroacetic acid (Sigma, Saint Louis, MO) containing 2 µmol of ferrous sulfate ($FeSO_4$; Sigma, Saint Louis, MO) and 100 µl of 0.67% thiobarbituric acid (Sigma, Saint Louis, MO) were added to each tube. Samples were incubated at 100° C. for 30 minutes and after cooling at 4° C. for 10 minutes, 200 µl of chloroform was added and samples were thoroughly mixed and centrifuged at 16,000×g for 10 min at 4° C. Supernatants were transferred to wells of a 96-well plate and 1 µl of 2% (in ethanol) of butylated hydroxyanisole (Sigma, Saint Louis, MO) was added to each well. Absorption was measure at 532 nm for samples and standards and the MDA concentration of each sample was determined by plotting its absorption on the standard curve. The bars represent the mean (±standard deviation). Statistical comparison was made by Student's unpaired t-test.

Serum SOD3. Serum SOD3 was measured by using an SOD3 ELISA kit (Abnova, Taipei, Taiwan) according to the manufacturer's instructions. Serum samples were from 7 patients with RP and 7 control patients. In brief, 100 µl of each serum sample or SOD3 standard was added to duplicate wells of a 96-well plate and incubated 2 hours at room temperature. After washing, 100 µl of working secondary antibody solution was added to each well and incubated for 1 hour at room temperature. After 3 washes, blocking solution was added to each well and the plate was incubated for 1 hour at room temperature. After 3 washes, primary antibody was added to each well and incubated for 1 hour at room temperature. After 3 washes, 100 µl of "working AV-HRP" solution was added to each well and the plate was incubated for 30 minutes at room temperature. Wells were washed 3 times, 100 µl of substrate was applied to each well, the plate was incubated at room temperature for 10 minutes and the reaction was stopped by adding 100 µl of stop solution. Absorbance at 450 nm was read on a plate reader. The readings from the standards were used to generate a standard curve and the SOD3 of each sample was determined by plotting its absorbance value on the standard curve. Each bar represents the mean (±standard deviation) SOD3 per ml of sample and statistical comparison was made by Student's unpaired t-test.

Figure 1:
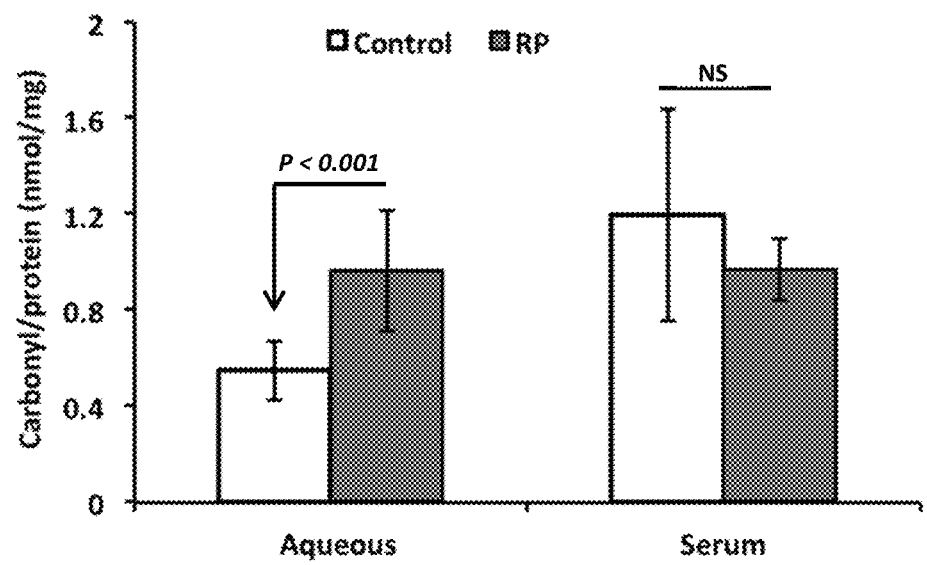
FIG. 1 is a graph that shows a comparison between retinitis pigmentosa (RP) patients and controls in carbonyl content of proteins in aqueous and serum. Aqueous samples from 9 RP and 9 control patients were assayed for protein carbonyl content and total protein. Control patients had macular pucker or macular hole, but no other eye diseases. Serum samples from 8 RP and 7 control patients were also assayed. Each bar represents the mean (±standard deviation) carbonyl content per mg total protein and statistical comparisons were made with Student's unpaired t-test.
Figure 2:
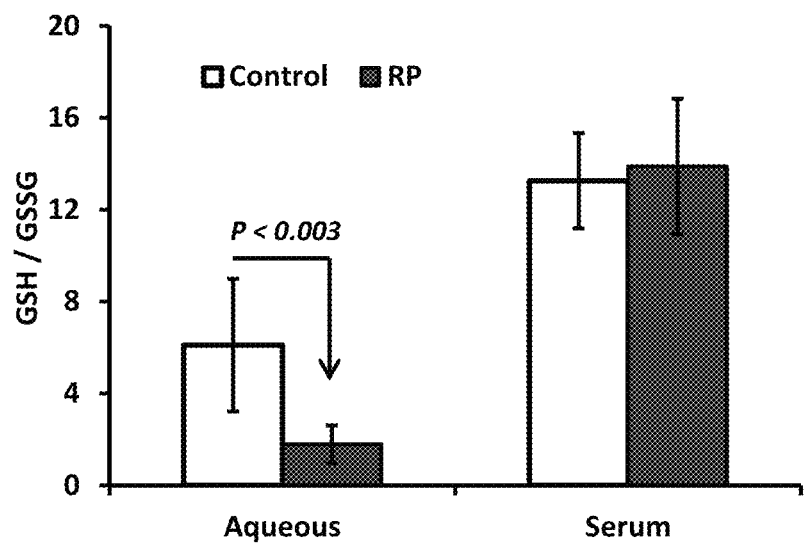
FIG. 2 is a graph that shows a comparison between retinitis pigmentosa (RP) patients and controls in reduced glutathione to oxidized glutathione ratio (GSH/GSSG) in aqueous and serum. Aqueous samples from 7 RP and 6 control patients and serum samples from 9 RP and 7 controls were assayed for GSH/GSSG ratio. The bars represent the mean (±standard deviation) GSH/GSSH ratio and statistical comparisons were made by Student's unpaired t-test.

Oxidative damage to proteins causes carbonyl groups to be introduced into side chains and ELISA for carbonyl adducts provides a quantitative measure of oxidative damage to proteins in a tissue. Compared to aqueous samples from control patients who were undergoing vitreous surgery for macular pucker or macular hole, aqueous samples from patients with RP had a significant elevation in mean carbonyl content of proteins (FIG. 1). There was no significant difference in carbonyl content of serum proteins in RP patients compared with controls. Oxidative damage to lipids results in lipid hydroperoxides that break down to form 4-hydroxynonenal, MDA, and acrolein. There was no significant difference in the mean level of MDA in the aqueous or serum of patients with RP compared to those of controls (FIG. 2).

Depletion of reduced glutathione in aqueous of RP patients. Reduced glutathione (GSH) is a major intracellular non-protein —SH compound and is the most important intracellular hydrophilic antioxidant. Under oxidative conditions, GSH is reversibly oxidized to glutathione disulfide (GSSG) and under reducing conditions, GSH is regenerated. Thus the GSH/GSSG ratio provides a measure of ongoing oxidative stress. The mean aqueous GSH/GSSG ratio was significantly reduced in patients with RP compared to controls, but there was no significant difference in the mean serum GSH/GSSG ratio (FIG. 3).

No difference in serum SOD3 levels in RP versus control patients. A previous study showed that compared to control patients, a group of patients with RP had a significant reduction in serum SOD3 levels. Thus, serum SOD3 levels was measured and found that in our patient population there was no significant difference between RP patients and controls (FIG. 4).

In mouse and pig models of RP, after rod photoreceptors die, there is progressive oxidative damage first to cones and then to cells of the inner retina. In this study, the present inventor demonstrate that human patients with RP also show evidence of ocular oxidative damage, because compared to control patients they have increased levels of proteins that have been subject to oxidative damage in aqueous humor. These patients also show evidence of ongoing oxidative stress because compared to controls, there significant depletion of reduced glutathione in aqueous humor. These data indicate that aqueous MDA levels are not altered in patients with RP. The oxidative stress in the eyes of patients with RP cannot be explained by a systemic problem that also affects the eyes, because there was no increase in oxidative damage to serum proteins nor was there a reduction in serum GSH/GSSG ratio. These data demonstrate ongoing oxidative stress and oxidative damage in the eyes of patients with RP.

The RP patients in this study had no difference in serum malondialdehyde (MDA) levels compared to controls suggesting that they did not have an increase in lipid peroxidation in the periphery. Compared to controls, the patients with RP in this study showed no significant increase in serum protein carbonyl content, showing that they did not have generalized oxidative damage to proteins throughout the body and there was no significant decrease in serum GSH/GSSG indicating against systemic oxidative stress. In this study, patients with RP had no significant reduction in serum SOD3 compared to controls.

Thus, it is likely that there may be something unusual about the population of RP patients studied in a previous report (Martinez-Fernandez de la Camara C, Salom D, Sequedo M D, Hervas D, Marin-Lambies C, Aller E, Jaijo T, Diaz-LLopis M, Millan J M, and Rodrigo R. Altered antioxidant-oxidant status in the aqueous humor and peripheral blood of patients with retinitis pigmentosa. *Plos One* 8: e74223: 1-8, 2013), because compared to controls, they had significant elevation of thiobarbituric acid reactive substances in serum suggesting an increase in oxidative damage to lipids throughout the body. Therefore, the RP patients included in the previous study may have had a systemic problem leading to widespread oxidative stress throughout the body, which makes any findings of the study difficult to interpret.

The present invention demonstrates that aqueous protein carbonyl content and GSH/GSSG ratio are biomarkers for disease activity in individual patients with RP. The present invention includes the measurement of aqueous protein carbonyl content and GSH/GSSG ratio in a clinical trial that tests the effect of antioxidant therapy on functional outcomes in patients with RP. The first step in this process is to determine if baseline aqueous protein carbonyl content is reduced and GSH/GSSG ratio increased by the therapy and if so, what percentage change in these parameters correlates with functional benefit. Validation of the parameters as biomarkers for disease activity would greatly facilitates the treatment of RP patients. For example, longitudinal studies in which serial measurements of aqueous protein carbonyl content and GSH/GSSG ratio are correlated with rate of reduction in visual fields and/or reduction in the length of ellipsoid zone on optical coherence tomography can also be conducted.

This study has demonstrated oxidative damage and ongoing oxidative stress in the aqueous humor of patient with RP supporting the hypothesis that oxidative stress participates in cone cell death in RP. This supports proceeding with a clinical trial to investigate the effects of potent antioxidants in patients with RP and suggests that aqueous protein carbonyl content and GSH/GSSG ratio should be tested as potential biomarkers.

All references, including publications, patent applications, and patents, cited herein are hereby incorporated by reference to the same extent as if each reference were individually and specifically indicated to be incorporated by reference and were set forth in its entirety herein.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for treating a subject having retinitis pigmentosa comprising:
   a) obtaining a biological sample from the subject;
   b) providing a control biological sample;
   c) measuring one or more of the following: cupric reducing antioxidant capacity, GSH/GSSG ratio, carbonyl adduct level in the sample of a) and b);
   d) comparing the one or more measurements of c) in the sample from the subject to the control sample;
   e) quantifying or staging the severity of the disease in the subject as progressing in stage, or increasing in severity, if the levels of cupric reducing antioxidant capacity and/or GSH/GSSG ratio is reduced relative to the control sample, and/or if the levels of carbonyl adduct level is elevated relative to the control sample; and
   f) selecting a course of treatment for the disease in the subject which is based on the stage or severity of disease indicated in e), wherein the treatment includes administering an effective treatment to the subject having retinitis pigmentosa, wherein the effective treatment comprises N-Acetylcysteine Amide (NACA).

2. The method of claim 1, wherein the sample is from the aqueous humor of the eye of the subject.

3. The method of claim 1, wherein the sample is from the blood or plasma of the subject.

4. A method for monitoring the treatment of a subject having retinitis pigmentosa comprising
   a) obtaining a biological sample from the subject;
   b) providing a control biological sample;
   c) measuring one or more of the following: cupric reducing antioxidant capacity, GSH/GSSG ratio, carbonyl adduct level, in the sample of a) and b);
   d) comparing the one or more measurements of c) in the sample from the subject to the control sample;
   e) determining the stage or the severity of disease in the subject, wherein if the levels of cupric reducing antioxidant capacity and/or GSH/GSSG ratio is reduced relative to the control sample, and/or if the levels of carbonyl adduct level is elevated relative to the control sample then the disease is identified as progressing in stage, or increasing in severity, or if the levels of cupric reducing antioxidant capacity and/or GSH/GSSG ratio is elevated relative to the control sample and/or if the levels of carbonyl adduct level is reduced relative to the control sample then the disease is identified as reducing in stage, or decreasing in severity of the retinitis pigmentosa;
   f) selecting a course of treatment for the disease in the subject which is based on the stage or severity of disease indicated in e), wherein the treatment includes administering an effective treatment to the subject having retinitis pigmentosa, wherein the effective treatment comprises N-Acetylcysteine Amide (NACA); and
   g) after administration of the course of treatment to the subject, repeating steps one or more times.

5. The method of claim 4, wherein the sample is from the aqueous humor of the eye of the subject.

6. The method of claim 4, wherein the sample is from the blood or plasma of the subject.

* * * * *